(12) United States Patent
Nishimi et al.

(10) Patent No.: US 8,303,896 B2
(45) Date of Patent: Nov. 6, 2012

(54) BIOSENSOR AND METHOD FOR IMMOBILIZING A PHYSIOLOGICALLY ACTIVE SUBSTANCE

(75) Inventors: Taisei Nishimi, Kanagawa (JP); Toshihide Ezoe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/848,280

(22) Filed: Aug. 2, 2010

(65) Prior Publication Data

US 2010/0324281 A1 Dec. 23, 2010

Related U.S. Application Data

(62) Division of application No. 11/709,026, filed on Feb. 22, 2007, now abandoned.

(30) Foreign Application Priority Data

Feb. 23, 2006 (JP) .................................. 2006-046270

(51) Int. Cl.
*G01N 33/53* (2006.01)
(52) U.S. Cl. ......... 422/82.01; 514/100; 435/23; 435/29; 435/7.1; 435/7.92; 435/6.1
(58) Field of Classification Search ............... 422/82.01; 435/6, 23, 29, 7.1, 7.92, 6.1; 514/100
See application file for complete search history.

(56) References Cited

U.S. PATENT DOCUMENTS

| 5,242,828 A | 9/1993 | Bergstroem et al. |
| 2006/0014232 A1 * | 1/2006 | Inagawa et al. ................. 435/23 |
| 2006/0110594 A1 | 5/2006 | Frutos et al. |

FOREIGN PATENT DOCUMENTS

| EP | 1 696 235 A | | 8/2006 |
| JP | 2002-062297 | | 2/2002 |
| JP | 2004170195 | * | 6/2004 |
| JP | 2004-357642 | | 12/2004 |
| JP | 2005-140590 | | 6/2005 |
| JP | 2005-221423 | | 8/2005 |
| JP | 2006-335912 A | | 12/2006 |
| JP | 2006-337219 A | | 12/2006 |
| WO | 03/075012 A | | 9/2003 |
| WO | 2004/046724 A | | 6/2004 |

OTHER PUBLICATIONS

Lindquist et al. (Analytical Biochemistry 198, 268-277 1991.*
Office Action dated Mar. 1, 2011 on Japanese Application No. JP 2007-040469.
Lahiri J et al: "A strategy for the generation of surfaces presenting ligands for studies of binding based on an active ester as a common reactive intermediate: a surface plasmon resonance study". Analytical Chemistry, American Chemical Society. Columbus, US, vol. 71, 1999, pp. 777-790, XP002229684, ISSN: 0003-2700.
Lofas S et al: "Methods for Site Controlled Coupling to Carboxymethyldextran Surfaces in Surface ' Plasmon Resonance Sensors". Biosensors & Bioelectronics, Elsevier, Science Publishers, Barking, GB, vol. 10, No. 9, 1995, pp. 813-822, XP000783535, ISSN: 0956-5663.
Lofas S et al: "A Novel Hydrogel Matrix on Gold Surfaces in Surface Plasmon Resonance Sensors for Fast and Efficient Covalent Immobilization of Ligands". Journal of the Chemical Society, Chemical Communications, Chemical Society. Letchworth, GB, No. 21, 1990, pp. 1526-1528, XP008050238.
Johnsson B et al: "Immobilization of Proteins to a Carboxymethyldextran-Modified Gold Surface for Biospecific Interaction Analysis in Surface Plasmon Resonance Sensors". Analytical Biochemistry, Academic Press, San Diego, CA, US, vol. 198, No. 2, 1991, pp. 268-277, XP008063693. ISSN: 0003-2697.
Linguist et al. (Analytical Biochemistry 198, 268-277 1991).
Yeung et al.(Journal of Chromatography A, 1073 (2005) 175-180.
Office Action dated Aug. 2, 2011 on Japanese Application No. JP 2007-040469.
Analytical Chemistry, vol. 76, No. 1, pp. 137-143 (Jan. 1, 2004).

* cited by examiner

*Primary Examiner* — Lyle Alexander
(74) *Attorney, Agent, or Firm* — Sughrue Mion, PLLC

(57) ABSTRACT

An object of the present invention is to provide a biosensor and a method for immobilizing a physiologically active substance, by which preconcentration effects can be obtained at a pH that is equivalent to or higher than the isoelectric point of the physiologically active substance and the physiologically active substance can be covalently bound to the surface. The present invention provides a biosensor comprising a solid substrate to which a polymer having a primary or secondary amino group is bound, by which a physiologically active substance can be chemically immobilized following preconcentration of the substance at a pH that is equivalent to or higher than the isoelectric point of the substance.

7 Claims, 3 Drawing Sheets

BIOSENSOR AND METHOD FOR IMMOBILIZING A PHYSIOLOGICALLY ACTIVE SUBSTANCE

This application is a divisional of application Ser. No. 11/709,026 filed Feb. 22, 2007, now abandoned.

TECHNICAL FIELD

The present invention relates to a biosensor and a method for immobilizing a physiologically active substance.

BACKGROUND ART

As a typical technique for immobilizing a physiologically active substance on an measurement chip, a method (amine coupling method) that involves binding an amino group of a physiologically active substance to a carboxyl group on a measurement chip is broadly used. This method requires dissolving a physiologically active substance in a buffer having a pH that is lower than the isoelectric point of such substance upon immobilization. Specifically, whereas a physiologically active substance will be positively charged when the pH is the isoelectric point of such substance or lower, a carboxyl group on a measurement chip is negatively charged from the alkali side through the acidic region with approximately pH 3.5. Therefore, a physiologically active substance is concentrated on a measurement chip due to electrostatic attraction. When such preconcentration is not performed, the amount of a physiologically active substance immobilized will drastically decrease. Thus, a physiologically active substance to be immobilized should be dissolved in a buffer having a pH that is lower than the isoelectric point of such substance, as disclosed in J. C. S. Chem. Commun., 1990, 1526 and U.S. Pat. No. 5,436,161.

This means that a physiologically active substance that is denatured under low-pH conditions is unable to be immobilized while maintaining its activity. Furthermore, a physiologically active substance such as an acidic protein has no positive net charge, even in the case of a pH of approximately 3.5. Thus, no preconcentration effects can be obtained, so that immobilization becomes impossible.

A physiologically active substance dissolved in a buffer having a pH that is higher than the isoelectric point of such substance can be immobilized on a solid surface because of electrostatic attraction between the substance and a cationic polymer immobilized on the solid surface. JP Patent Publication (Kokai) No. 8-245815 A (1996) discloses a technique using such principle, which involves alternately layering a protein and an organic polymer ion.

This method is very good in that a physiologically active substance can be conveniently immobilized. However, two problems arise in view of application to a biosensor. The first problem is that because binding between a protein and a substrate depends only on electrostatic interaction, a part of the physiologically active substances that have been electrostatically adsorbed on a solid surface may be dissociated due to a washing step using an acidic solution or an alkaline solution. The second problem is that a physiologically active substance is obtained in the form of a densely packed monomolecular layer. To increase the amount of a physiologically active substance immobilized, it is desirable to three-dimensionally immobilize a physiologically active substance. Furthermore, dense packing of a physiologically active substance is not preferable in terms of application to a biosensor for assaying binding and dissociation behaviors of compounds interacting with the physiologically active substance.

DISCLOSURE OF INVENTION

In view of such circumstances, an object to be achieved by the present invention is to provide a biosensor and a method for immobilizing a physiologically active substance, by which preconcentration effects can be obtained at a pH that is equivalent to or higher than the isoelectric point of the physiologically active substance and the physiologically active substance can be covalently bound to the surface.

As a result of intensive studies to achieve the above object, the present inventors have discovered that preconcentration effects can be obtained in the case of a solution containing a physiologically active substance and having a pH that is equivalent to or higher than the isoelectric point of such substance by using a surface having thereon a primary or secondary amino group. Furthermore, the present inventors have also discovered that the physiologically active substance can be immobilized on the surface via covalent bonding through contact with a carboxylic acid activator under such conditions. Thus the present inventors have completed the present invention.

The present invention provides a biosensor comprising a solid substrate to which a polymer having a primary or secondary amino group is bound, by which a physiologically active substance can be chemically immobilized following preconcentration of the substance at a pH that is equivalent to or higher than the isoelectric point of the substance.

Another aspect of the present invention provides a method for immobilizing a physiologically active substance, which comprises preconcentrating a physiologically active substance having a carboxyl group at a pH that is equivalent to or higher than the isoelectric point of the substance, on a solid substrate to which a polymer having a primary or secondary amino group is bound, causing a carboxylic acid activator to come into contact with the substrate, so as to bind the polymer having the amino group to the physiologically active substance.

Preferably, the polymer having a primary or secondary amino group is a polymer obtained by causing a polymer having a carboxyl group to react with a polyamine.

Preferably, the polymer having the carboxyl group is carboxymethyldextran.

Preferably, the solid substrate to which the polymer having the primary or secondary amino group is bound is a solid substrate to which a water-soluble polymer is bound, a solid substrate to which a hydrophobic polymer is bound, or a solid substrate on which a self-assembled monomolecular film is formed.

Preferably, a layer of the polymer having the primary or secondary amino group is formed on a metal.

Preferably, the metal is gold, silver, copper, platinum, or aluminium.

Preferably, the biosensor according to the present invention is used for nonelectrochemical detection.

Preferably, the biosensor according to the present invention is used for surface plasmon resonance analysis.

Further another aspect of the present invention provides a method for detecting or measuring a substance that interacts with a physiologically active substance, which comprises a step of causing a test substance to come into contact with the biosensor according to the present invention as mentioned above, on the surface of which a physiologically active substance is covalently bound.

Preferably, a substance that interacts with a physiologically active substance is detected or measured by a nonelectrochemical method.

Preferably, a substance that interacts with a physiologically active substance is detected or measured by surface plasmon resonance analysis.

BEST MODE FOR CARRYING OUT THE INVENTION

Figure 1:
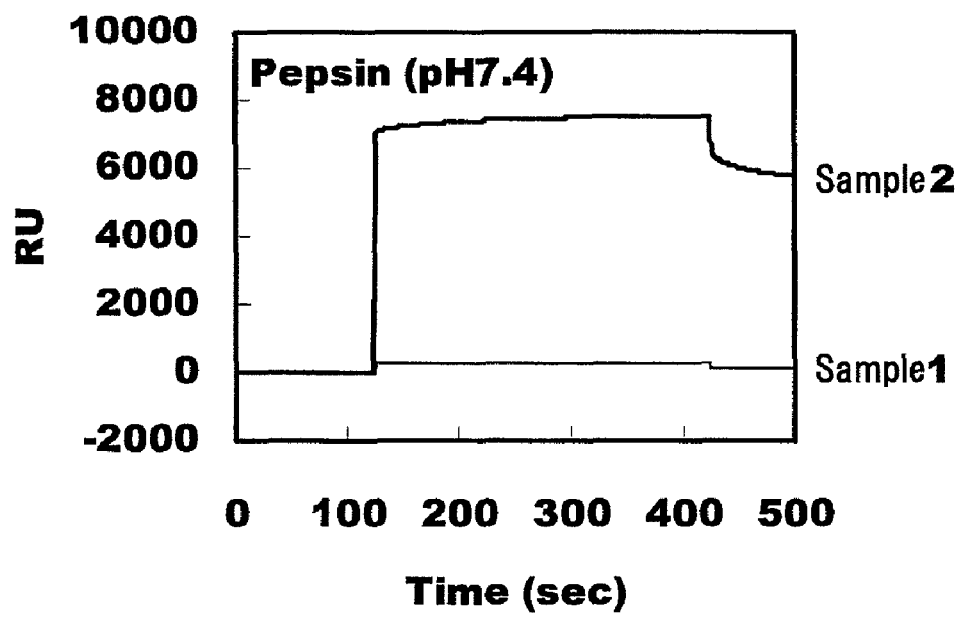
FIG. 1 shows a sensorgram obtained by setting sample 1 (comparative example) and sample 2 (the present invention) prepared in Example 1 in a surface plasmon measurement device and then applying a pepsin solution (pH 7.4) for 5 minutes.

The embodiments of the present invention will be described below. Hereinafter, the embodiments of the present invention will be described in detail. Furthermore, in the present invention, when a numerical value represents the value of a physical property, the value of a characteristic, or the like, "(numerical value 1) to (numerical value 2)" means "(numerical value 1) or more and (numerical value 2) or less."

The biosensor of the present invention is characterized by: having a surface that has thereon a primary or secondary amino group so that preconcentration effects can be obtained in the case of a solution containing a physiologically active substance and having a pH that is equivalent to or higher than the isoelectric point of such substance; and being capable of immobilizing the physiologically active substance on the surface via covalent bonding through contact with a carboxylic acid activator under such conditions.

The surface having thereon a primary or secondary amino group is preferably a self-assembled monomolecular film surface, a hydrophobic polymer-bound surface, or a water-soluble polymer-bound surface. A water soluble polymer-bound surface is most preferable in view of its ability to three-dimensionally immobilize a physiologically active substance.

A self-assembled monomolecular film will be explained. Sulfur compounds such as thiol and disulfides are spontaneously adsorbed onto a noble metal substrate such as gold, providing a monomolecular-sized ultra thin film. Furthermore, such assembly is referred to as a self-assembled film, because it is shown to have sequences depending on the crystal lattice of a substrate or the molecular structure of admolecules. Examples of the self-assembled monomolecular film include alkanethiols on gold surfaces, alkylsilanes on glass surfaces, and alcohols on silicon surfaces. Specific examples of alkanethiols that can be used herein include 7-carboxy-1-heptanethiol, 10-carboxyl-decanethiol, 4,4'-dithiobutyric acid, and 11-hydroxy-1-undecanethiol, 11-amino-1-undecanethiol. In the present invention, the hydrophobic polymers or water-soluble polymers listed below may be bound to a self-assembled monomolecular film on a substrate.

The hydrophobic polymer which can be used in the present invention is a polymer having no or low water-absorbing properties. Its solubility in water (at 25° C.) is 10% or less, more preferably 1% or less, and most preferably 0.1% or less.

Specific examples of the hydrophobic polymer include a polyacrylic acid derivative, a polymethacrylic acid derivative, polyethylene (PE), polypropylene (PP), polybutadiene, polymethylpentene, cycloolefin polymer, polystyrene (PS), acrylonitrile/butadiene/styrene copolymer (ABS), styrene/maleic anhydride copolymer/polyvinyl chloride (PVC), polyethylene terephthalate (PET), polyethylene naphthalate (PEN), nylon 6, nylon 66, cellulose acetate (TAC), polycarbonate (PC), modified polyphenylene ether (m-PPE), polyphenylene sulfide (PPS), polyether ketone (PEK), polyether ether ketone (PEEK), polysulfone (PSF), polyether sulfone (PES), polyphenylene sulfide (PPS), and liquid crystal polymer (LCP). Preconcentration and binding of a physiologically active substance with a pH that is equivalent to or higher than the isoelectric point of such substance to a two-dimensional surface are also made possible, when a reactive group capable of chemically immobilizing a physiologically active substance and a cationic group are introduced on the surface of the above hydrophobic polymer.

A substrate can be coated with a hydrophobic polymer according to common methods. Examples of such a coating method may include spin coating, air knife coating, bar coating, blade coating, slide coating, curtain coating, spray method, evaporation method, cast method, and dip method.

Examples of a water-soluble polymer include natural polymers such as a dextran derivative, a starch derivative, a cellulose derivative, and gelatin, and synthetic polymers such as polyvinyl alcohol, polyethylene glycol, polyvinyl pyrrolidone, a polyacrylamide derivative, and polymethylvinylether. When a cationic group is introduced at a high rate, the previously described hydrophobic polymer will be a water-soluble polymer. In view of application to a biosensor, natural water-soluble polymers are preferable and dextran derivatives are particularly preferable.

Water-soluble polymers bound to a surface form three-dimensional hydrogel. Introduction of a reactive functional group into such three-dimensional hydrogel enables three-dimensional immobilization of a physiologically active substance as disclosed in U.S. Pat. No. 5,436,161. Compared with immobilization on a two-dimensional surface, three-dimensional immobilization is extremely advantageous in view of application to a biosensor, because the binding amount of a physiologically active substance is increased. Based on such viewpoint, it is preferable in the present invention to immobilize a physiologically active substance using three-dimensional hydrogel comprising a primary or secondary amino group.

In the present invention, a polymer having a primary or secondary amino group, being capable of chemically immobilizing a physiologically active substance, is used after preconcentration of the physiologically active substance at a pH that is equivalent to or higher than the isoelectric point of such substance.

Methods for introducing functional groups into polymers that are used in the present invention are also not particularly restricted. A polymer may also be produced by performing a polymerization reaction of monomers having a primary or secondary amino group. Alternatively, a polymer may be previously produced and then a primary or secondary amino group may be introduced by a so-called polymer reaction.

Examples of a monomer containing a primary amino group, which can be used in the present invention, include aminomethyl(meth)acrylate, aminoethyl(meth)acrylate, aminopropyl(meth)acrylate, aminobutyl(meth)acrylate, p-aminostyrene, and allylamine. Examples of a monomer containing a secondary amino group, which can be used in the present invention, include monomethylaminoethyl(meth) acrylate, N-methyl(meth)acrylamide, N-ethyl(meth)acrylamide, N-methylolacrylamide, and N-(4-anilinophenyl)methacrylamide.

A polymer to be used in the present invention may be produced through copolymerization of monomer components other than monomers having a primary or secondary amino group. Examples of such monomer components other than the monomers having a primary or secondary amino group to be used in the present invention include the following monomers:
acrylic esters, methacrylic acid esters, and amides of ethylene unsaturated carboxylic acid (e.g., acrylamide, methacrylamide, N-acryloyl morpholine, and N,N-dimethylacrylamide, 2-acrylamide-2-methylpropane sulfonic acid (or a salt thereof)); aromatic monomers (e.g., styrene, vinyltoluene, p-t-butylstyrene, and vinylnaphthalene); other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinyl acetoamide, acrylonitrile, and methacrylonitrile); monomers having nonionic groups (e.g., 2-hydroxyethylacrylate, 2-hydroxyethyl methacrylate, hydroxypropylacrylate, hydroxypropylmethacrylate, 2-hydroxy-3-chloropropylacrylate, β-hydroxyethyl-β'-acryloyloxyethylphthalate, 1,4-butylene glycol monoacrylate, hydroxystyrene, allylalcohol, methallyl alcohol, isopropenyl alcohol, and 1-butenyl alcohol); and monomers having dipolar ionic groups (e.g., [2-(methacryloyloxy)ethyl]dimethyl-(3-sulfopropyl)ammonium hydroxide, and [2-(methacryloyloxy)ethyl] phosphorylcholine).

Specific examples of a water-soluble polymer having a primary or secondary amino group that is used in the present invention include chitosan, polylysine, polyethyleneimine, polyvinylamine, and polyallylamine.

Another water-soluble polymer having a primary or secondary amino group, which can also be preferably used in the present invention, is obtained by activating a water-soluble polymer having a carboxyl group and then causing the activated polymer to react with a polyamine. Specific examples of such polyamine that can preferably be used herein include: aliphatic diamines such as ethylenediamine, tetraethylenediamine, octamethylene diamine, decamethylene diamine, piperazine, triethylenediamine, diethylenetriamine, triethylenetetraamine, dihexamethylene triamine, and 1,4-diamino cyclohexane; aromatic diamines such as paraphenylenediamine, methaphenylene diamine, paraxylylenediamine, metaxylylenediamine, 4,4'-diamonobiphenyl, 4,4'-diamino diphenylmethane, 4,4'-diamino diphenylketone, and 4,4'-diaminodiphenyl sulfonic acid; and polyamines such as diethylenetriamine, triethylenetetramine, tetraethylenepentamine, pentaethylenehexamine, spermidine, spermin, and polyethyleneimine. In view of improvement of hydrophilicity of the biosensor surface, a compound (formula 1) wherein 2 amino groups are linked with an ethylene glycol unit can also be used.

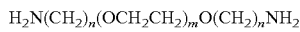

$$H_2N(CH_2)_n(OCH_2CH_2)_mO(CH_2)_nNH_2 \qquad 1$$

As a polymer containing a carboxyl group that is used in the present invention, a synthetic polymer containing a carboxyl group and a natural polymer containing a carboxyl group can be used. Examples of such synthetic polymer containing a carboxyl group include polyacrylic acid, and polymethacrylic acid, as well as copolymers thereof. Specific examples of such copolymer include a methacrylic acid copolymer, an acrylic acid copolymer, an itaconic acid copolymer, a crotonic acid copolymer, a maleic acid copolymer, a partially esterified maleic acid copolymer, and a copolymer obtained by adding an acid anhydride to a polymer having a hydroxy group, as disclosed in the descriptions of JP Patent Publication (Kokai) No. 59-44615 A (1984), JP Patent Publication (Kokoku) No. 54-34327 B (1979), JP Patent Publication (Kokoku) No. 58-12577 B (1983), JP Patent Publication (Kokoku) No. 54-25957 B (1979), JP Patent Publication (Kokai) No. 59-53836 A (1984), and JP Patent Publication (Kokai) No. 59-71048 A (1984). Such natural polymers containing carboxyl groups may be natural plant extracts, microbial fermentation products, enzymatically synthesized products, or chemically synthesized products. Specific examples of such natural polymers include: polysaccharides such as hyaluronic acid, chondroitin sulfuric acid, heparin, dermatan sulfate, carboxymethylcellulose, carboxyethylcellulose, cellouronic acid, carboxymethylchitin, carboxymethyldextran, and carboxymethyl starch; and polyamino acids such as polyglutamic acid and polyaspartic acid. Commercially available compounds can be used as natural polysaccharides containing carboxyl groups. Specific examples of such commercially available compounds include: carboxymethyldextrans such as CMD, CMD-L, and CMD-D40 (produced by Meito Sangyo Co., Ltd.); sodium carboxymethylcellulose (produced by Wako Pure Chemical Industries, Ltd.); and sodium alginate (produced by Wako Pure Chemical Industries, Ltd.).

A polymer containing a carboxyl group is preferably a polysaccharide containing a carboxyl group and more preferably carboxymethyldextran.

The molecular weight of a polymer containing a carboxyl group that may be used in the present invention, is not particularly limited. The average molecular weight of such polymer preferably ranges from 1,000 to 5,000,000, more preferably ranges from 10,000 to 2,000,000, and further preferably ranges from 100,000 to 1,000,000. When the average molecular weight is below such range, the amount of a physiologically active substance immobilized becomes smaller. When the average molecular weight is above such range, handling thereof becomes difficult due to high solution viscosity.

A known technique can be preferably used as a method for activating polymers containing carboxyl groups. Examples of such method include: a method that involves activating carboxyl groups using 1-(3-Dimethylaminopropyl)-3 ethylcarbodiimide (EDC) (water-soluble carbodiimide) and N-Hydroxysuccinimide (NHS); a method disclosed in JP Patent Application No. 2004-238396 (JP Patent Publication (Kokai) No. 2006-58071A) (specifically, the method involves activating carboxyl groups using any one of compounds including a uronium salt, a phosphonium salt, and a triazine derivative having a specific structure); and a method disclosed in JP Patent Application No. 2004-275012 (JP Patent Publication (Kokai) No. 2006-90781A) (specifically, the method involves performing activation using a carbodiimide derivative or a salt thereof, followed by activation of carboxyl groups using any one of compounds including a nitrogen-containing heteroaromatic compound having a hydroxyl group, a phenol derivative having an electron-withdrawing group, and an aromatic compound having a thiol group). It becomes possible to produce the biosensor surface of the present invention by causing a polymer containing a carboxyl group that has been activated by these techniques to react with a polyamine.

It is generally known that mixture of polyanions such as water-soluble polymers having carboxyl groups and polycations such as water-soluble polyamines in water results in the generation of water-insoluble polyion complexes. Therefore, it is desirable in the present invention to cause a water-soluble polymer having a carboxyl group to react with a water-soluble polyamine without any solvent or in a water-insoluble solvent.

A method for immobilizing a physiologically active substance is provided according to the present invention, which comprises causing a solution containing a physiologically active substance and having a pH that is equivalent to or higher than the isoelectric point of such substance to come into contact with a surface having thereon a primary or secondary amino group and then causing a carboxylic acid activator to come into contact with such surface. In the above immobilization method of the present invention, the primary or secondary amino group introduced onto the aforementioned surface makes it possible to obtain preconcentration effects by which a physiologically active substance is concentrated on the surface of an assay chip due to electrostatic attraction, even when a solution containing the physiologically active substance and having a pH that is equivalent to or higher than the isoelectric point of such substance is caused to come into contact with such surface.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor of the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

In the biosensor obtained as mentioned above, a physiologically active substance is covalently bound via an amino group present on the surface, so that the physiologically active substance can be immobilized on metal surface or metal film.

A physiologically active substance is allowed to come into contact with the surface of the biosensor of the present invention, so that the physiologically active substance is covalently bound with an amino group present on the surface of the biosensor. Thus, the physiologically active substance can be immobilized on the biosensor.

A physiologically active substance immobilized in the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenaline esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection-angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta$SP), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta$SP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta$SP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta$SP) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta$SP) is measured periodically after the elapse of a certain time, and it is determined whether or not a change has occurred in the above attenuated total reflection angle ($\theta$SP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta$SP). For example, a sample solution may be added to a sensing substance, and the amount of an attenuated total reflection angle ($\theta$SP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle ($\theta$SP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle ($\theta$SP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

This example relates to preparation of a sensor chip for immobilizing proteins.
(1) Preparation of Sample 1 (Comparative Example)
A Biacore sensor chip CM-5 (research grade) was used as a surface to which carboxymethyl dextran had been bound.
(2) Preparation of Sample 2 (the Present Invention)
100 μl of a 1:1 mixed solution of a 2.8 mM HODhbt (3,4-dihydro-3-hydroxy-4-oxo-1,2,3-benzotriazine) aqueous solution and a 0.4M EDC aqueous solution was caused to come into contact with the surface of a Biacore sensor chip CM-5 (research grade), followed by 10 minutes of reaction at room temperature. The surface was washed with water and then dried at room temperature for 10 minutes using a vacuum dryer. 100 μl of 1,2-bis(2-aminoethoxy)ethane was caused to come into contact with the surface, followed by 10 minutes of reaction at room temperature and then washing with water. The surface of interest was thus obtained.

Example 2

This Example relates to preconcentration of proteins having pHs that are equivalent to or higher than the isoelectric points on a surface (sample 2) modified with 1,2-bis(2-amino ethoxy)ethane. Proteins used herein were pepsin (produced by Wako Pure Chemical Industries, Ltd.), BSA (Bovine Serum Albumin: produced by SIGMA), and CA (Carbonic Anhydrase: produced by SIGMA).

Figure 2:
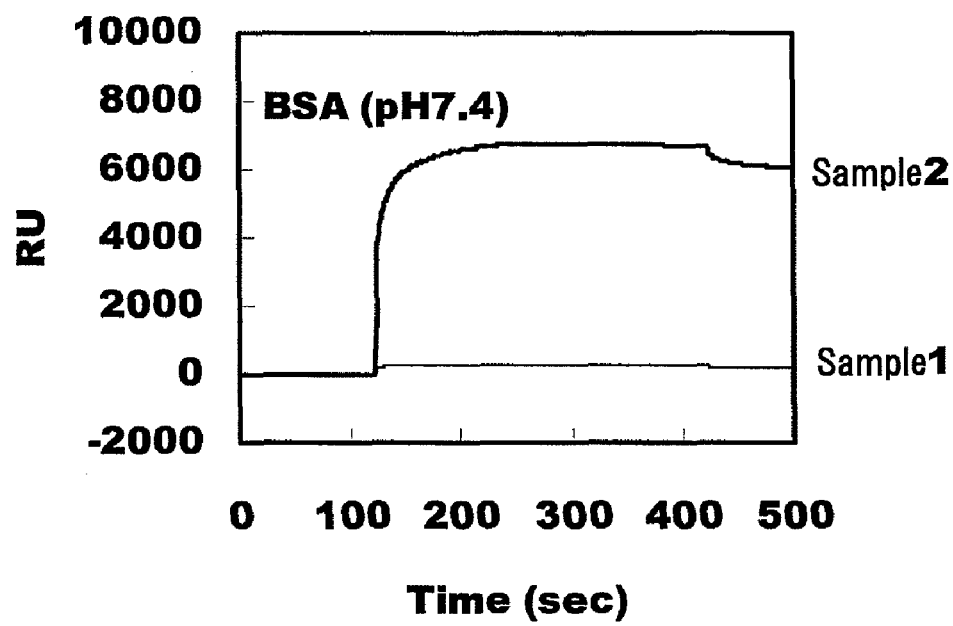
FIG. 2 shows the sensorgram obtained by setting sample 1 (comparative example) and sample 2 (the present invention) prepared in Example 1 in a surface plasmon resonance device and then applying a BSA solution (pH7.4) for 5 minutes.
Figure 3:
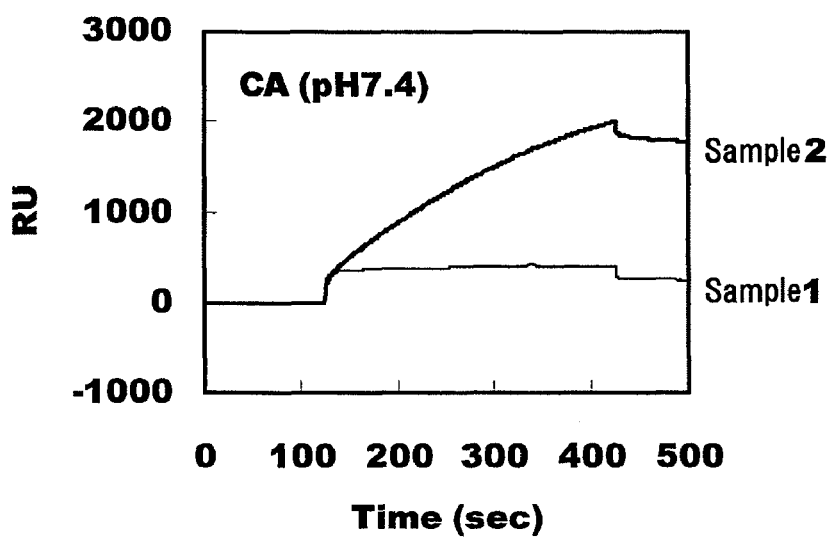
FIG. 3 shows the sensorgram obtained by setting sample 1 (comparative example) and sample 2 (the present invention) prepared in Example 1 in a surface plasmon resonance device and then applying a CA solution (pH7.4) for 5 minutes.

Sample 1 (comparative example) and the sample 2 (the present invention) prepared in Example 1 were set in a Biacore 3000 (a surface plasmon resonance device produced by Biacore). Preconcentration was examined by applying each protein solution (pH7.4, 1.0 mg/ml) for 5 minutes. FIGS. 1 to 3 show the thus obtained sensorgrams.

In the case of sample 1 to which carboxymethyl dextran had been bound, no proteins were observed to have been preconcentrated thereon. In contrast, in the case of sample 2 of the present invention, all proteins were observed to have been preconcentrated thereon. The degrees of the preconcentration were confirmed to indicate pepsin (7520 RU), BSA (6688 RU), and CA (1958 RU), respectively. It was thus demonstrated that preconcentration of CA is possible at a pH that is equivalent to or higher than the isoelectric point due to the nature of the surface of the present invention having thereon a primary amino group.

Example 3

Figure 4:
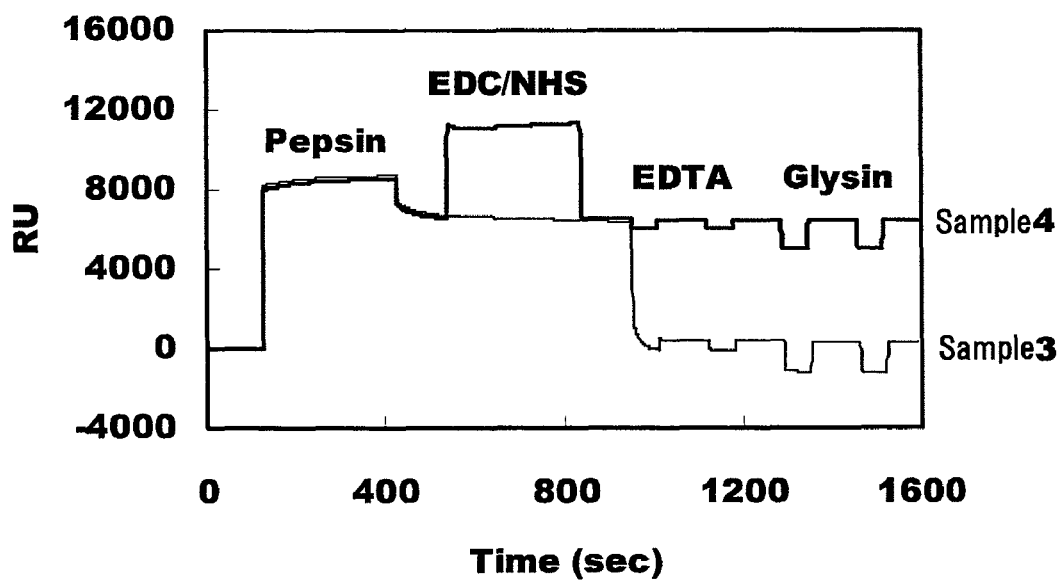
FIG. 4 shows the results obtained through examination of: the amount of pepsin immobilized on sample 3 prepared by washing without allowing an EDC (0.4 M)/NHS (0.1 M) aqueous solution (carboxylic acid activator) to come into contact with sample 2 upon which pepsin (pH 7.4) had been preconcentrated for 5 minutes; and the amount of pepsin immobilized on sample 4 prepared by washing after causing an EDC (0.4M)/NHS (0.1 M) aqueous solution to come into contact with sample 2 and remain in contact therewith for 5 minutes.

This Example relates to immobilization of proteins preconcentrated on the surface having thereon a primary amino group. Sample 3 was prepared by washing without allowing an EDC (0.4 M)/NHS (0.1 M) aqueous solution (a carboxylic acid activator) to come into contact with sample 2, upon which pepsin (1 mg/ml, pH 7.4) had been preconcentrated for 5 minutes. Sample 4 was prepared by washing after causing an EDC (0.4 M)/NHS (0.1 M) aqueous solution to come into contact with sample 2 and remain in contact therewith for 5 minutes. The amounts of pepsin immobilized on samples 3 and 4 were examined using Biacore 3000. Washing was performed through injection of a 1% EDTA aqueous solution (1 minute×2) and a glycine buffer (pH 1.5, produced by Biacore) (1 minute each×2). FIG. 4 shows the thus obtained results.

It was confirmed that after washing, preconcentrated pepsin had been dissociated from the surface (sample 4) that had been prepared by washing without contact with the carboxylic acid activator. In contrast, even after washing, approximately 6000 RU of pepsin was confirmed to remain bound to the surface (sample 5) with which the carboxylic acid activator had been caused to come into contact. It was thus demonstrated that a polymer having an amino group can be bound to a protein by preconcentrating the protein at a pH that is equivalent to or higher than the isoelectric point of such protein upon a solid substrate to which the polymer having a primary amino group had been bound and then causing a carboxylic acid activator to come into contact with the substrate.

Example 4

This Example relates to preparation of sensor chips modified with polyamines other than 1,2-bis(2-aminoethoxy) ethane. Samples 5 to 9 were prepared by performing procedures similar to those used in preparation of sample 2, except that polyamines listed in Table 1 were used instead of 1,2-bis (2-aminoethoxyethane).

TABLE 1

| | Diamine | Remarks |
| --- | --- | --- |
| Sample 1 | None | Comparative example |
| Sample 2 | 1,2-bis(2-aminoethoxyethane) | The present invention |
| Sample 5 | Ethylenediamine | The present invention |
| Sample 6 | Diethylenetriamine | The present invention |
| Sample 7 | Triethylenetetramine | The present invention |
| Sample 8 | Tetraethylenepentamine | The present invention |
| Sample 9 | Pentaethylenehexamine | The present invention |

Example 5

Figure 5:
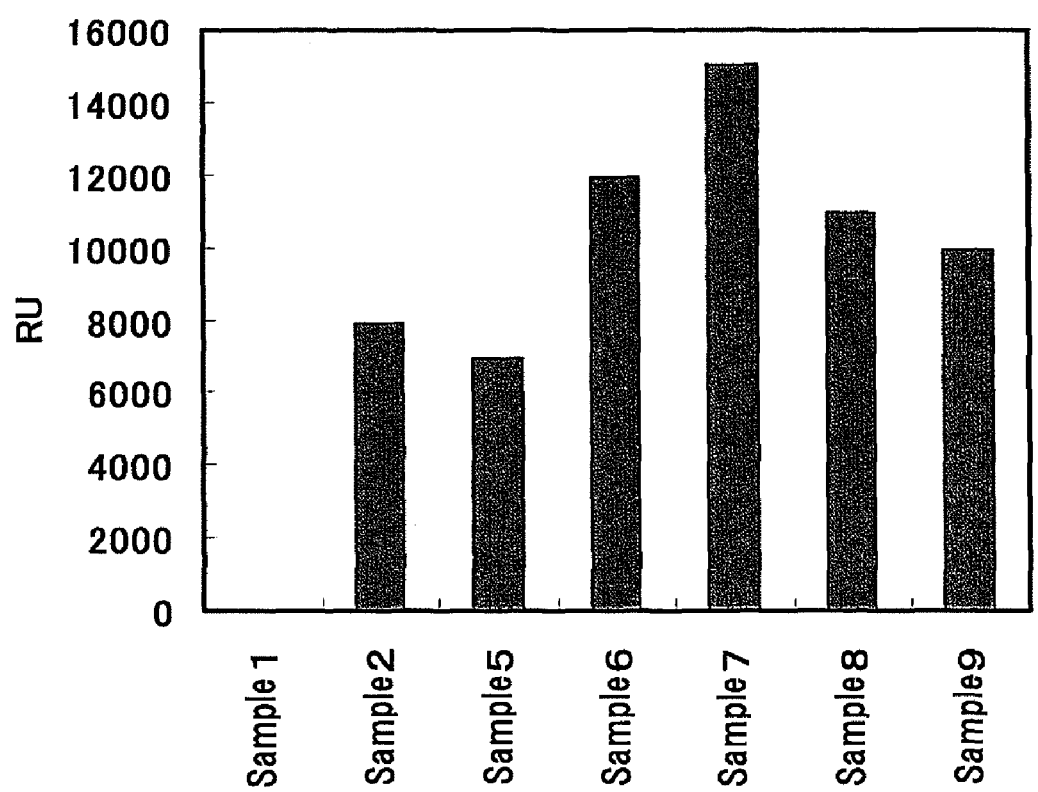
FIG. 5 shows the results obtained through examination of the preconcentration degrees of BSA (pH 7.4, 0.1 mg/ml) on sensor chips prepared using various polyamines.

This Example relates to charge concentration of proteins upon the sensor chips prepared in Example 4. The degrees of preconcentration of BSA (pH 7.4, 0.1 mg/ml) upon samples 5 to 9 were examined by the method described in Example 2. The thus obtained results are summarized in FIG. 5.

Preconcentration was observed under conditions of pH 7.4 that is equivalent to or higher than the isoelectric point of BSA not only in the case of sample 2 with 1,2-bis(2-aminoethoxyethane) bound thereto as a polyamine, but also in the cases of sample 5 with ethylenediamine bound thereto, sample 6 with diethylenetriamine bound thereto, sample 7 with triethylenetetramine bound thereto, sample 8 with tetraethylenepentamine bound thereto, and sample 9 with pentaethylenehexamine bound thereto. It was demonstrated that the degrees of preconcentration depend on the relevant types of polyamines.

EFFECTS OF THE INVENTION

According to the biosensor of the present invention, even when a solution containing a physiologically active substance and having a pH that is equivalent to or higher than the isoelectric point of such substance is used, preconcentration effects (whereby a physiologically active substance is concentrated on an assay chip due to electrostatic attraction) can be obtained, and the physiologically active substance can be immobilized on the biosensor surface via covalent bonding.

The invention claimed is:
1. A method for immobilizing a physiologically active substance, which comprises:
preconcentrating a physiologically active substance having a carboxyl group at a pH that is equivalent to or higher than the isoelectric point of the physiologically active substance, on a solid substrate to which a polymer having a primary or secondary amino group is bound; and
causing a carboxylic acid activator to come into contact with the substrate, so as to bind the polymer having the amino group to the physiologically active substance,
wherein the polymer having the primary or secondary amino group is a polymer obtained by causing a polymer having a carboxyl group to react with a polyamine, wherein the polyamine is at least one selected from the group consisting of 1,2-bis(2-aminoethoxy)ethane, ethylenediamine, tetraethylenediamine, octamethylene diamine, decamethylene diamine, piperazine, triethylenediamine, diethylenetriamine, triethylenetetraamine, dihexamethylene triamine, 1,4-diamino cyclohexane, paraphenylenediamine, methaphenylene diamine, paraxylylenediamine, metaxylylenediamine, 4,4'-diaminobiphenyl, 4,4'-diamino diphenylmethane, 4,4'-diamino diphenylketone, 4,4'-diaminodiphenyl sulfonic acid, diethylenetriamine, triethylenetetramine, tetraethylene- pentamine, pentaethylenehexamine, spermidine, spermin, and polyethyleneimine.

2. The method for immobilizing a physiologically active substance according to claim 1, wherein the polymer having the carboxyl group is carboxymethyldextran.

3. The method for immobilizing a physiologically active substance according to claim 1, wherein the solid substrate to which the polymer having the primary or secondary amino group is bound is a solid substrate to which a water-soluble polymer is bound, a solid substrate to which a hydrophobic polymer is bound, or a solid substrate on which a self-assembled monomolecular film is formed.

4. The method for immobilizing a physiologically active substance according to claim 1, wherein a layer of the polymer having the primary or secondary amino group is formed on a metal.

5. The method for immobilizing a physiologically active substance according to claim 4, wherein the metal is gold, silver, copper, platinum, or aluminium.

6. The method for immobilizing a physiologically active substance according to claim 1, wherein the polymer having the carboxyl group is a polysaccharide containing a carboxyl group.

7. The method for immobilizing a physiologically active substance according to claim 1, wherein the polyamine is at least one selected from the group consisting of diethylenetriamine, triethylenetetraamine, tetraethylenepentamine, and pentaethylenehexamine.

* * * * *